(12) United States Patent
Ferree

(10) Patent No.: US 9,737,343 B2
(45) Date of Patent: Aug. 22, 2017

(54) FASTENING ASSEMBLIES FOR DISC HERNIATION REPAIR AND METHODS OF USE

(71) Applicant: Suture Concepts Inc., Basking Ridge, NJ (US)

(72) Inventor: Bret A. Ferree, Cincinnati, OH (US)

(73) Assignee: Suture Concepts Inc., Basking Ridge, NJ (US)

( * ) Notice: Subject to any disclaimer, the term of this patent is extended or adjusted under 35 U.S.C. 154(b) by 0 days.

(21) Appl. No.: 14/256,447

(22) Filed: Apr. 18, 2014

(65) Prior Publication Data

US 2015/0088205 A1    Mar. 26, 2015

Related U.S. Application Data

(63) Continuation of application No. 11/805,677, filed on May 23, 2007, now Pat. No. 8,702,733.

(Continued)

(51) Int. Cl.
| | |
|---|---|
| *A61F 2/44* | (2006.01) |
| *A61B 17/70* | (2006.01) |
| *A61B 17/04* | (2006.01) |
| *A61B 17/80* | (2006.01) |
| *A61F 2/30* | (2006.01) |

(52) U.S. Cl.
CPC ...... *A61B 17/7053* (2013.01); *A61B 17/0401* (2013.01); *A61B 17/7059* (2013.01); *A61F 2/442* (2013.01); *A61B 17/8085* (2013.01); *A61F 2002/3008* (2013.01); *A61F 2002/30062* (2013.01); *A61F 2002/30448* (2013.01); *A61F 2002/30451* (2013.01); *A61F 2002/30461* (2013.01); *A61F 2002/30462* (2013.01); *A61F 2002/30578* (2013.01); *A61F 2002/30917* (2013.01); *A61F 2002/30932* (2013.01); *A61F 2002/4435* (2013.01); *A61F 2002/4495* (2013.01); *A61F 2210/0004* (2013.01); *A61F 2220/005* (2013.01);

(Continued)

(58) Field of Classification Search
CPC ............... A61F 2002/4435; A61F 2002/4495
See application file for complete search history.

(56) References Cited

U.S. PATENT DOCUMENTS

| | | | |
|---|---|---|---|
| 6,093,205 A * | 7/2000 | McLeod et al. | 623/17.16 |
| 6,878,167 B2 | 4/2005 | Ferree | |

(Continued)

*Primary Examiner* — Eduardo C Robert
*Assistant Examiner* — Atiya Mahmud
(74) *Attorney, Agent, or Firm* — Pandiscio & Pandiscio

(57) ABSTRACT

Devices and methods for fixing defects in the anulus fibrosus (vertebral disc) of a patient are described. The devices include a mesh patch, and first and second suture assemblies, each of which include an anchor and a suture. The anchor has a first portion adapted to be inserted into a bone and a second portion having an opening therethrough. The suture is adapted to be disposed through the opening and has a first end is adapted to couple to the mesh patch. The method of treatment includes inserting the first portion of the first anchor into a cranial vertebra and inserting the second portion of the second anchor into a caudal vertebra. The first ends of the sutures are attached to the mesh patch. The mesh patch is positioned adjacent the defect by pulling on, or applying tension to, the second ends of the sutures.

10 Claims, 17 Drawing Sheets

Related U.S. Application Data

(60) Provisional application No. 60/808,795, filed on May 26, 2006.

(52) U.S. Cl.
CPC .......... *A61F 2220/0058* (2013.01); *A61F 2220/0075* (2013.01); *A61F 2250/0098* (2013.01)

(56) References Cited

U.S. PATENT DOCUMENTS

| | | |
|---|---|---|
| 7,201,774 B2 | 4/2007 | Ferree |
| 2003/0009227 A1* | 1/2003 | Lambrecht et al. ....... 623/17.16 |
| 2003/0195514 A1* | 10/2003 | Trieu et al. .................... 606/61 |
| 2004/0260397 A1 | 12/2004 | Lambrecht et al. |
| 2005/0143826 A1 | 6/2005 | Zucherman et al. |
| 2005/0209639 A1* | 9/2005 | Gidwani et al. ............. 606/228 |
| 2005/0216087 A1* | 9/2005 | Zucherman et al. ...... 623/17.16 |
| 2006/0089646 A1* | 4/2006 | Bonutti ........................ 606/61 |
| 2006/0149380 A1* | 7/2006 | Lotz et al. ................. 623/17.12 |
| 2006/0247776 A1 | 11/2006 | Kim |
| 2006/0247784 A1* | 11/2006 | Kim ........................... 623/17.16 |
| 2006/0252980 A1* | 11/2006 | Arnal ................ A61B 17/0401 600/29 |
| 2007/0150064 A1 | 6/2007 | Ruberte et al. |
| 2007/0198021 A1 | 8/2007 | Wales |
| 2008/0172071 A1 | 7/2008 | Barker |

* cited by examiner

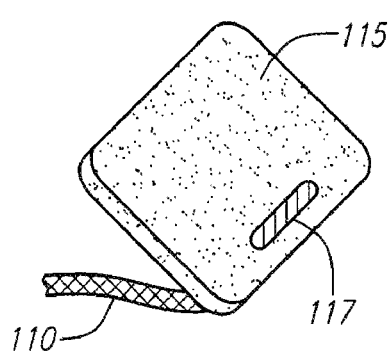
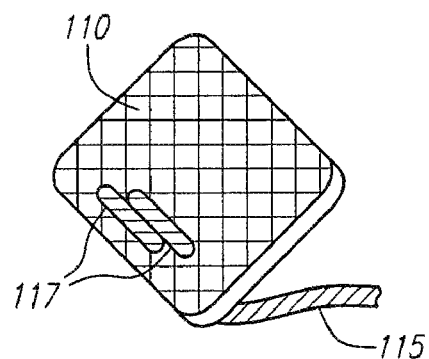
FIG. 7A
FIG. 7B
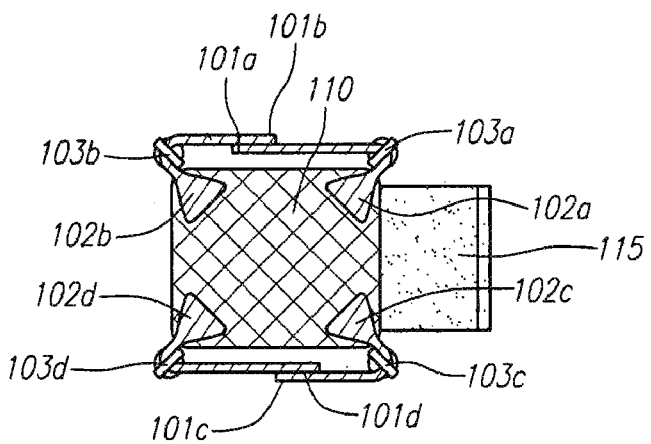
FIG. 7C
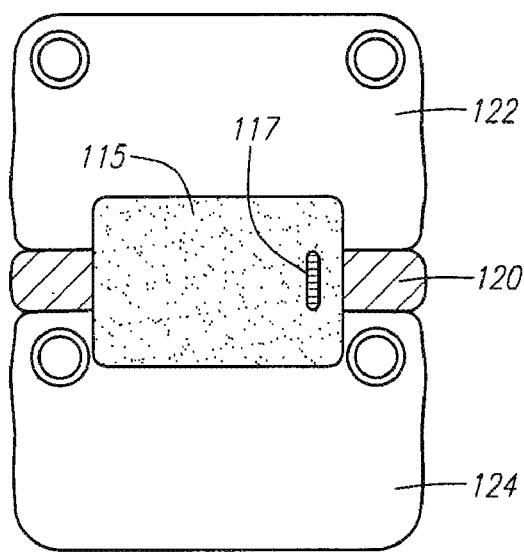
FIG. 7D
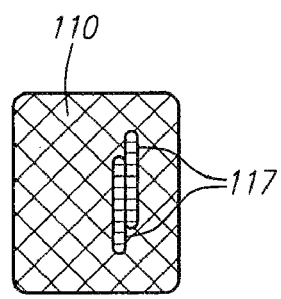
FIG. 7E

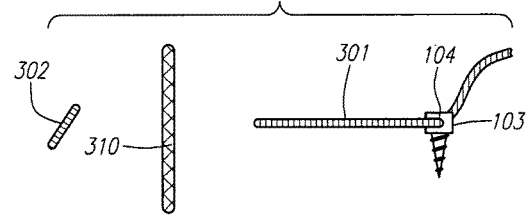
FIG. 16A
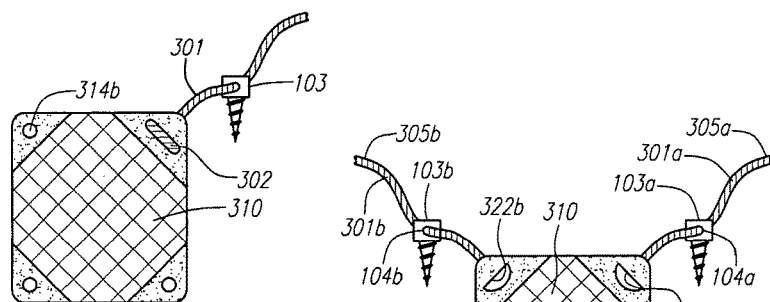
FIG. 16B
FIG. 17
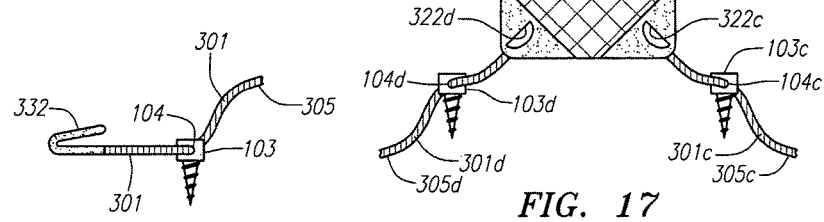
FIG. 18A
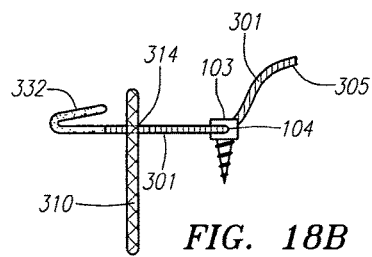
FIG. 18B
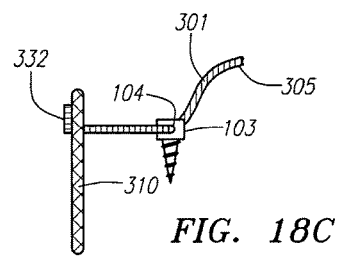
FIG. 18C

FASTENING ASSEMBLIES FOR DISC HERNIATION REPAIR AND METHODS OF USE

RELATED APPLICATIONS

This patent application is a continuation of pending prior U.S. patent application Ser. No. 11/805,677, filed May 23, 2007by Bret A. Ferree for FASTENING ASSEMBLIES FOR DISC HERNIATION REPAIR AND METHODS OF USE, which in turn claims the benefit of prior U.S. patent application Ser. No. 60/808,795, filed May 26, 2006, entitled "Fastening Assemblies for Disc Herniation Repair and Methods of Use." This patent application is also related to U.S. patent application Ser. Nos. 60/748,518, filed Dec. 8, 2005, entitled "Cemented Sutures" and 60/738,833, filed Nov. 21, 2005, entitled "Sub-PLL Annular Repair Methods and Devices." All of the above-mentioned applications are hereby expressly incorporated by reference in their entirety.

FIELD OF THE INVENTION

The subject invention resides in methods and apparatus for reconstructing the anulus fibrosus (AF) of a spinal disc and the ligaments of the spine. The invention is particularly well suited to the prevention of extrusion of material or devices placed into the disc space and to the prevention of excessive spinal motion.

BACKGROUND

The human intervertebral disc is an oval to kidney bean-shaped structure of variable size depending on the location in the spine. The outer portion of the disc is known as the anulus fibrosus (AF). The anulus fibrosus is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The anulus fibers become redundant as the nucleus shrinks. The redundant annular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete anular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. patent application Ser. No. 10/407,554 and U.S. Pat. No. 6,878,167, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often applies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY

In one aspect of the invention, devices for fixing a defect in the anulus fibrosus of a patient are provided. The devices include a mesh patch, a first suture assembly, and a second suture assembly. The first suture assembly includes a first anchor and a first suture. The first anchor has a first portion adapted to be inserted into a bone and a second portion having an opening therethrough. The first suture has a first end and a second end, wherein the first suture is disposed through the hole in the first anchor and wherein the first end is capable of being coupled to the mesh patch. Similarly, the second suture assembly has a second anchor and a second suture. The second anchor has a first portion adapted to be inserted into a bone and a second portion having an opening therethrough. The second suture has a first end and a second end, wherein the second suture is disposed through the hole in the second anchor and wherein the first end is capable of being coupled to the mesh patch.

The sutures may be attached to the mesh patch by welding the first ends of the first and second sutures to the mesh patch. The ends that are attached to the mesh patch may include an enlarged surface area; e.g., the enlarged surface area may be longer or wider than a diameter of the suture. Alternatively, the first ends of the sutures may include a transverse element adapted to anchor the first ends to the mesh patch. The sutures may be slidably disposed within the opening of its respective anchor. Alternatively, the suture may be fixedly attached to its respective anchor. The device may further include third and fourth suture assemblies, each of which has an anchor and suture as described above. The device may also include an anti-adhesion cover adapted to be connected to the mesh patch.

In another aspect of the invention, a method of treating a defect in a vertebral disc of a patient is described. The method includes the steps of providing a device that includes a mesh patch, a first suture assembly, and a second suture assembly, as described above. The first portion of the first anchor is inserted into a vertebra cranial to the vertebral disc. The first portion of the second anchor is inserted into a vertebra caudal to the vertebral disc. The first ends of the first and second sutures are attached to the mesh patch. The mesh patch is positioned adjacent the defect by pulling on, or applying tension to, the second ends of the first and second sutures. The method may further include the step of placing an anti-adhesion cover adjacent the mesh patch.

The first ends of the first and second sutures may be attached to the mesh patch by welding. Alternatively, the first ends of the sutures may comprise a transverse element and the mesh patch may have openings, and the sutures may be attached to the mesh patch by inserting the first ends of the sutures through the openings such that the transverse elements are positioned on a side of the mesh patch opposite of the second ends of the sutures. For instance, a longitudinal axis of the transverse element may be substantially perpendicular to a longitudinal axis of the suture near the first end. The second ends of the first and second sutures may be anchored, e.g., by attaching the second end of the first suture to the second end of the second suture. In one embodiment, the second ends may be anchored or attached together by welding. Third and fourth suture assemblies may also be provided. The first portion of the third anchor may be inserted into the vertebra cranial to the disc and the first portion of the fourth anchor may be inserted into the vertebra caudal to the disc. The first ends of the third and fourth sutures may be attached to the mesh patch and the mesh patch can then be positioned adjacent the defect by pulling on, or applying tension to, the second ends of the third and fourth sutures.

In another aspect of the invention, a device for fixing a defect in the anulus fibrosus of a patient is described. The device includes a mesh patch, first and second sutures, and first and second anchors. The first and second sutures each have a first end and a second end, wherein the first end is adapted for coupling to the mesh patch. The first and second anchors each have a first portion adapted for insertion into a bone and a second portion having an opening, wherein the opening of the first anchor is adapted to receive the first suture and the opening of the second anchor is adapted to receive the second suture. The device may optionally include third and fourth sutures and third and fourth anchors, similar to the first and second sutures and anchors described above.

The sutures may be attached to the mesh patch by welding the first ends of the first and second sutures to the mesh patch. The ends that are attached to the mesh patch may include an enlarged surface area, e.g., the enlarged surface area may be longer or wider than a diameter of the suture. Alternatively, the first ends of the sutures may include a transverse element adapted to anchor the first ends to the mesh patch. The sutures may be slidably disposed within the opening of its respective anchor. Alternatively, the suture may be fixedly attached to its respective anchor. The device may further include third and fourth suture assemblies, each of which has an anchor and suture as described above. The device may also include an anti-adhesion cover adapted to be connected to the mesh patch.

In another aspect of the invention, a method for treating a defect in a vertebral disc of a patient is described. The method includes providing a device having a mesh patch, first and second sutures, and first and second anchors. The first and second sutures each have a first end and a second end, wherein the first end is capable of being coupled to the mesh patch. The first and second anchors each have a first portion adapted to be inserted into a bone and a second portion having an opening, wherein the first suture is threaded through the opening of the first anchor and the second suture is threaded through the opening of the second anchor. The first portion of the first anchor is inserted into a vertebra cranial to the vertebral disc. The first portion of the second anchor is inserted into a vertebra caudal to the vertebral disc. The first ends of the first and second sutures are attached to the mesh patch. The mesh patch is positioned adjacent the defect by pulling on, or applying tension to, the second end of the first and second sutures. The method may further include the step of placing an anti-adhesion cover adjacent the mesh patch.

The first ends of the first and second sutures may be attached to the mesh patch by welding. Alternatively, the first ends of the sutures may comprise a transverse element and the mesh patch may have openings, and the sutures may be attached to the mesh patch by inserting the first ends of the sutures through the openings such that the transverse elements are positioned on a side of the mesh patch opposite of the second ends of the sutures. For instance, a longitudinal axis of the transverse element may be substantially perpendicular to a longitudinal axis near the first ends. The second ends of the first and second sutures may be anchored, e.g., by attaching the second end of the first suture to the second end of the second suture. In one embodiment, the second ends may be anchored or attached together by welding. Third and fourth sutures and third and fourth anchors may also be provided, similar to the first and second anchors described above. The first portion of the third anchor may be inserted into the vertebra cranial to the disc and the first portion of the fourth anchor may be inserted into the vertebra caudal to the disc. The first ends of the third and fourth sutures may be attached to the mesh patch and the mesh patch can then be positioned adjacent the defect by pulling on, or applying tension to, the second ends of the third and fourth sutures.

In another aspect of the invention, a device for fixing a defect in the anulus fibrosus of a patient is described. The device includes a mesh patch; first, second, third, and fourth sutures; and first, second, third, and fourth anchors. The first, second, third, and fourth sutures each have a first end and a second end, wherein the first end is adapted for coupling to the mesh patch. The first, second, third, and fourth anchors each have a first portion adapted for insertion into a bone and a second portion having an opening, wherein the openings of the first, second, third, and fourth anchors are adapted to receive the first, second, third, and fourth sutures.

Each of the sutures may be attached to the mesh patch by welding the first ends of the first and second sutures to the mesh patch. The ends that are attached to the mesh patch may include an enlarged surface area, e.g., the enlarged surface area may be longer or wider than a diameter of the suture. Alternatively, the first ends of the sutures may include a transverse element adapted to anchor the first ends to the mesh patch. The sutures may be slidably disposed within the opening of its respective anchor. Alternatively, the suture may be fixedly attached to its respective anchor. The device may further include third and fourth suture assemblies, each of which has an anchor and suture as described above. The device may also include an anti-adhesion cover adapted to be connected to the mesh patch.

In another aspect of the invention, a method for treating a defect in a vertebral disc of a patient is described. The method includes providing a device having a mesh patch; first, second, third, and fourth sutures; and first, second, third, and fourth anchors, as described above. The first portions of the first and second anchors are inserted into a vertebra cranial to the vertebral disc. The first portions of the third and fourth anchors are inserted into a vertebra caudal to the vertebral disc. The first ends of the first, second, third, and fourth sutures are attached to the mesh patch. The mesh patch is positioned adjacent the defect by pulling on, or applying tension to, the second end of the first, second, third, and fourth sutures.

The first ends of the first and second sutures may be attached to the mesh patch by welding. Alternatively, the first ends of the sutures may comprise a transverse element and the mesh patch may have openings, and the sutures may be attached to the mesh patch by inserting the first ends of the sutures through the openings such that the transverse elements are positioned on a side of the mesh patch opposite of the second ends of the sutures. For instance, a longitudinal axis of the transverse element may be substantially perpendicular to a longitudinal axis near the first ends. The second ends of the first and second sutures may be anchored, e.g., by attaching the second end of the first suture to the second end of the second suture. In one embodiment, the second ends may be anchored or attached together by welding. Third and fourth sutures and third and fourth anchors may also be provided. The first portion of the third anchor may be inserted into the vertebra cranial to the disc and the first portion of the fourth anchor may be inserted into the vertebra caudal to the disc. The first ends of the third and fourth sutures may be attached to the mesh patch and the mesh patch can then be positioned adjacent the defect by pulling on, or applying tension to, the second ends of the third and fourth sutures.

BRIEF DESCRIPTION OF FIGURES

FIG. 7A is an oblique view of an alternative embodiment of the invention with an anti-adhesion cover fastened to the mesh patch at or near an edge of mesh patch.

FIG. 7B is an oblique view of the undersurface of the embodiment of the invention drawn in FIG. 7A.

FIG. 7C is a posterior view of an anti-adhesion cover connected or coupled to a mesh device along an edge, where the mesh patch has been connected to anchors with welded sutures.

FIG. 7D is a posterior view of a coronal cross section of the spine and the embodiment of the invention drawn in FIG. 7C.

FIG. 7E is a view of the undersurface of the mesh patch drawn in FIG. 7D.

FIG. 16A is an exploded lateral view of an alternative embodiment of the invention drawn in FIG. 15C.

FIG. 16B is a posterior view of the embodiment of the invention drawn in FIG. 16A.

FIG. 17 is a posterior view of an alternative embodiment of the invention drawn in FIG. 16B wherein four sutures with enlargements at the first ends of the sutures are passed through eyelets in the corners of the mesh patch and then passed through eyelets in the anchors.

FIG. 18A is a lateral view of an alternative embodiment of a suture anchor wherein one end of the suture has a deformable component.

FIG. 18B is a lateral view of a mesh patch with the deformable end of the suture passed through an opening in the mesh patch.

FIG. 18C is a lateral view of the embodiment of the invention drawn in FIG. 18B where the deformable component prevents the suture from pulling out of the mesh patch.

DETAILED DESCRIPTION

Materials could be placed into the defective region or regions of the Annulus Fibrosus (AF) to promote healing across the entire thickness of the defective region of the AF. For example, a clot of blood marrow aspirated from the vertebrae or other bone in the skeleton could be injected into and over the defective region of the AF. The marrow aspirate could also be injected into and over the in-growth mesh patch or sheet. The cells of the marrow aspirate could be concentrated using such systems as the "Harvest Select" system by DePuy spine. Alternative materials, such as fibrin glue ("Tisseal", Baxter), or other bio-glue could be inserted into and/or over the defective region of the AF. Portions of the vertebrae near the defective region of the AF, could be perforated, for example with a 1-2 mm diameter drill bit or bur, to improve the blood supply to the relatively avascular AF. The holes are preferably drilled through the vertebral endplates (VEPs) near the defective region of the AF.

The invention may seal the defective region of the AF to promote healing on one side of the device and to prevent anti-adhesion materials from entering the defective region of the AF. Additionally, anti-adhesion materials such Coseal (Baxter) could be injected over the device.

Figure 1:
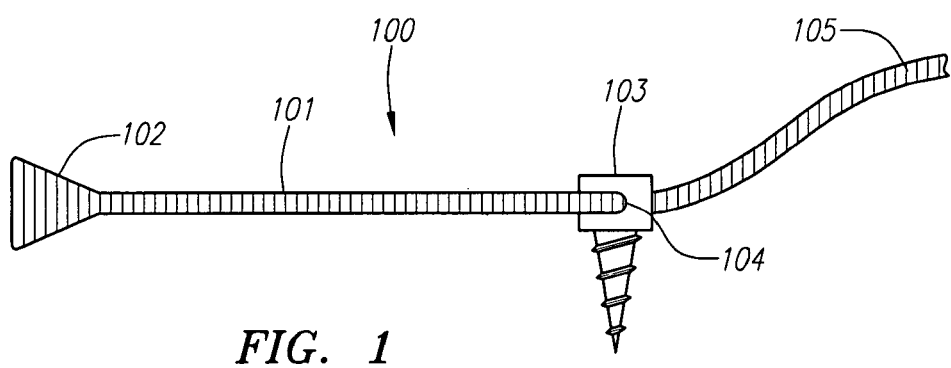
FIG. 1 is a lateral view of a suture anchor.

FIG. 1 is a lateral view of suture anchor 100. Suture anchor 100 comprises suture 101 with a flattened end 102 and screw (or anchor) 103. Anchor 103 has a first portion capable of being inserted into or otherwise attached to a bone, such as a vertebrae. Anchor 103 also has a second portion with an opening 104 adapted to receive a suture therethrough. In one embodiment, anchor 103 is a screw having a hole through the head of screw. Suture 101 is threaded through hole 104. Suture 101 is preferably made of polyester or other weldable material and has a break-strength of greater than about 22 lbs. Screw or anchor 103 is preferably about 3 mm in diameter, alternatively about 4 mm in diameter, and between about 5 mm and about 10 mm in length. However, alternative sized sutures or screws may be used with this invention. Anchors 103 are preferably made of a MRI compatible and radio-opaque material such as Titanium. Plastic or bioresorbable anchors may also used with this invention. Anchors 103 are preferably self-drilling and self-tapping.

Figure 2A:
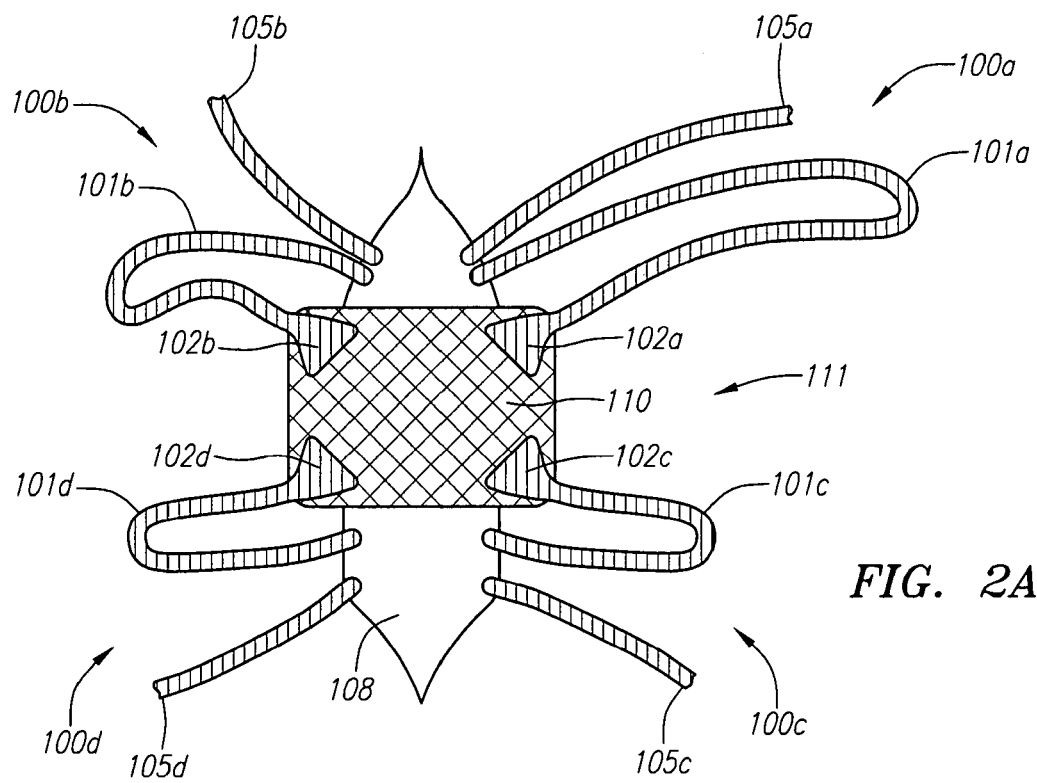
FIG. 2A is a posterior view of a surgical incision and an attached mesh device.

FIG. 2A is a posterior view of a surgical incision and a mesh device 111, attached thereto. Mesh device 111 has four suture anchors 100a-d coupled to mesh patch (or mesh sheet) 110. Screws 103 (or anchors) are located underneath/behind the surgical incision 108. The size of mesh patch 110 will depend on the defect being treated. In one embodiment, the size may be between about 5 and about 45 mm in width, and between about 5 and about 25 mm in height. The shape of mesh patch 110 will also depend on the defect being treated. The mesh patches could be supplied to surgeons in various sizes and shapes. Alternatively, surgeons could cut the mesh patch and anti-adhesion cover at the time of surgery. Mesh patch 110 may be a symmetrical or an asymmetrical shape. Shapes of mesh patch 110 may include, but not be limited to, a rectangle, a square, a polygon, a circle, an ellipse, an oval, a planar disc, and a triangle. Flattened ends 102a-b of sutures 101a-d have been attached to the corners of mesh patch 110. In one embodiment, flattened ends 102a-b may be attached by welding. Mesh patch 110 is preferably made of polyester or other material with pores of approximately 1 mm in diameter, alternatively approximately 1.5 mm in diameter, alternatively approximately 2.0 mm in diameter, or any other pore size that will facilitate tissue in-growth. Mesh patch 110 is preferably less than 1 mm thick and has a burst strength of greater than 738 kPa and a break-strength of greater than 400 N. Additionally, mesh patch 110 is preferably inelastic. For example, mesh patch 110 could have a break elongation % (ASTM D-5034) of at least 112 MD and 109 CMD. Mesh patch 110 may also include reinforced areas (not shown). Mesh patch 110 preferably overlaps the intact AF and/or the vertebrae by at least 2 mm, alternatively by at least 2.5 mm, alternatively by at least 3.0 mm, alternatively by at least 3.5 mm, alternatively by at least 4.0 mm, alternatively by at least 4.5 mm, alternatively by at least 5.0 mm, alternatively by at least 5.5 mm, alternatively by at least 6.0 mm, in one or more directions around the defect or surgical incision.

In use, sutures 101a-d are preferably welded or otherwise attached to mesh patch 110 after threading the anchors 103 into the vertebrae. Sutures 101a-d may be welded or otherwise attached to mesh patch 110 outside surgical wound 108. The break-strength of the weld (or attachment) between the flattened end 102a-d of sutures 101a-d and mesh patch 110 preferably exceeds 22 lbs. Free ends 105a-d of sutures 101a-d may then be pulled in order to bring mesh patch 110 flush against the defect.

Alternatively, flat ends 102a-d of sutures 101a-d may be attached to mesh patch 110 prior to inserting anchors 103, or other fastening members, to the spine. Anchors 103 may be forced into the vertebrae rather than threaded into the vertebrae in the alternative embodiment of the invention. The anchors may include deployable components that lock the anchors into the vertebrae. The anchors or fixation members do not pass through the mesh in either embodiment of the device.

Sutures 101a-d may be attached to mesh patch 110 in numerous ways. As discussed previously, flattened ends 102a-d may be welded to the corners of mesh patch 110 using a welding tool. The materials could be welded with a tool from Axya Medical (Beverly, Mass.). The welding tool could weld one suture at a time to the mesh patch. The mesh could be treated to increase the strength of the weld to the sutures. For example, the mesh could be abraided, treated with acid, or an adhesive material to strengthen the weld. Alternatively, more than one suture could be welded to the mesh patch simultaneously. The ends of the sutures could also be fastened to the mesh in other manners. For example, the ends of the sutures could be passed through holes in the mesh and welded to the sutures to create loops at the ends of the sutures (not shown).

Figure 2B:
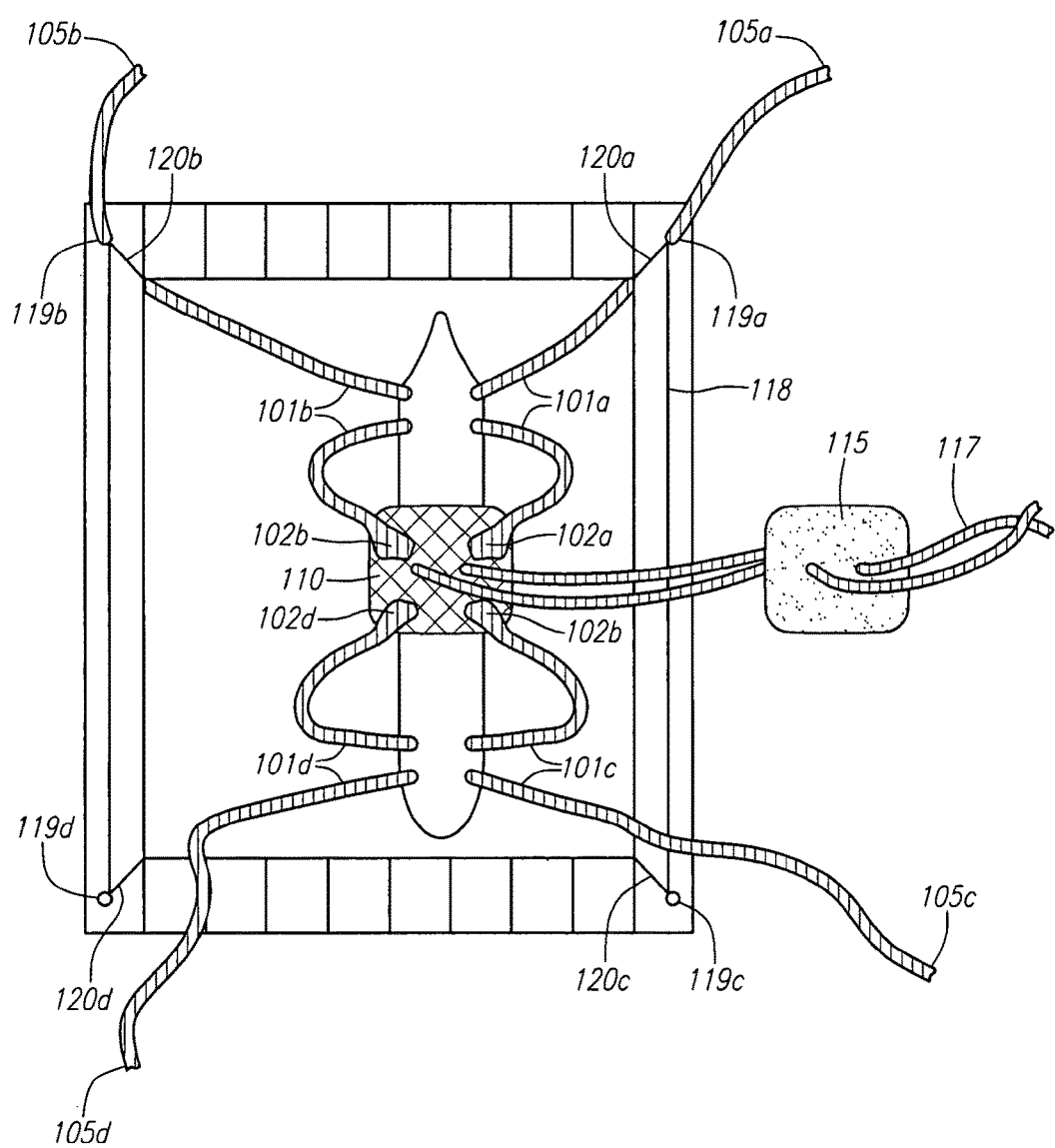
FIG. 2B is a posterior view of a surgical incision, a mesh device, a suture holding instrument, and an anti-adhesion cover.

FIG. 2B is a posterior view of a surgical incision and an alternative embodiment of a mesh device comprising the embodiment of the invention drawn in FIG. 2A, a suture holding instrument, and an anti-adhesion cover. Anti-adhesion cover 115 is made of a material that discourages tissue in-growth or adhesions. For example, anti-adhesion cover 115 may be made of ePTFE, Sepratfilm, allograft, or absorbable materials. These absorbable materials include oxidized atelocollagen type I, polyethylene glycol, glycerol, or combinations thereof. Anti-adhesion cover 115 will have interstitial pore sizes of 3 microns or less to discourage tissue in-growth. Anti-adhesion cover 115 will have a larger size than mesh patch 110. Anti-adhesion cover 115 may have a symmetrical or asymmetrical shape. Shapes of anti-adhesion cover 115 may include, but not be limited to, a rectangle, a square, a polygon, a circle, an ellipse, an oval, a planar disc, and a triangle. This will enable complete coverage of welded sutures 101a-d and anchors 103a-d once it is deployed, thereby discouraging tissue in-growth and adhesions from outside the wound site. Anti-adhesion cover 115 is loosely connected to mesh patch 110 by a loop (not shown) of suture 117. This loose connection through suture 117 allows anti-adhesion cover 115 to be moved away from mesh patch 110 while sutures 101a-d are welded or otherwise fastened to mesh patch 110. In one embodiment, suture 117 may be passed through reinforced sections of mesh patch 110. After sutures 101a-d have been attached to mesh patch 110, anti-adhesion cover 115 may be brought into contact with mesh patch 110 by sliding anti-adhesion patch 115 along suture 117 towards mesh patch 110. Mesh patch 110 may be brought into contact with the wound by pulling free ends 105a-d of sutures 101a-d either before or after anti-adhesion device is brought into contact with mesh patch 110.

Free ends 105a-d of sutures 101a-d may be held away from the wound site until needed using suture holding instrument 118, which is preferably made of an elastomeric material. Free ends 105a-b of the top two sutures are held in openings 119a-b in the corners of suture holding instrument 118. Free ends 105c-d of the bottom two sutures have not yet been placed into holes 119c-d in the bottom of suture holding instrument 118. Suture holding instrument 118 is designed to allow more movement of sutures 101a-d within holes 119a-d of the device than within slits 120a-d leading to holes 119a-d of the device. Holes 119a-d of the device may accommodate both ends of each suture. Surgeons may use the tool to organize the ends of the sutures during surgical procedures.

Figure 3A:
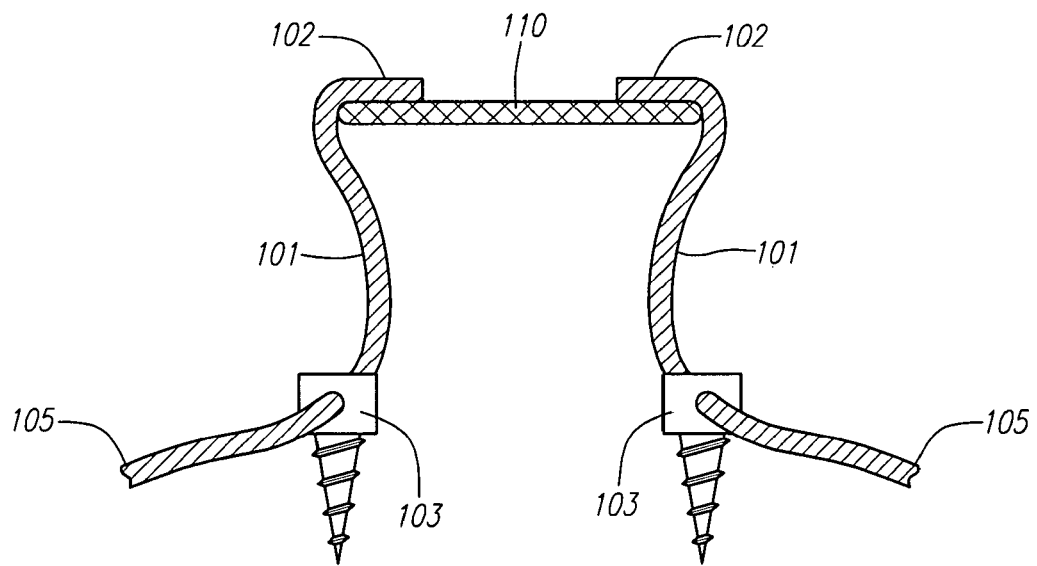
FIG. 3A is lateral view of a mesh patch and two suture anchors.

FIG. 3A is lateral view of mesh patch 110 and two suture anchors 101. Flattened ends 102 of the sutures have been welded or otherwise attached to the corners of mesh patch 110. Flattening the ends of the sutures increases the weldable surface area and reduces the profile of the assembled device.

Figure 3B:
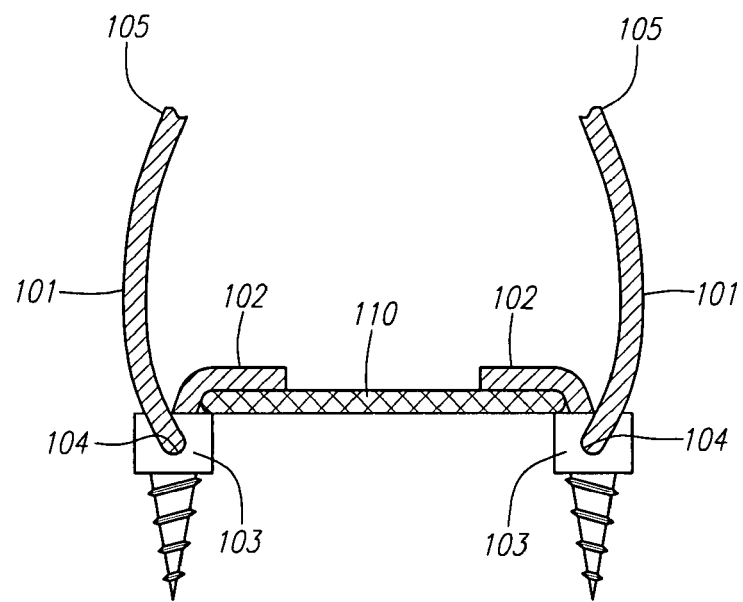
FIG. 3B is a lateral view of the embodiment of the invention drawn in FIG. 3A, with the mesh patch advanced towards the anchors.

FIG. 3B is a lateral view of the embodiment of the invention drawn in FIG. 3A. Mesh patch 110 is advanced towards anchors 103 by pulling on free ends 105 of the sutures. The eyelets 104 in anchors 103 are designed to minimize injury to the suture as sutures 101 are advanced through eyelets 104. Multifilament sutures are also used to further reduce the risk of damaging the sutures as the sutures are advanced through the eyelets.

Figure 4:
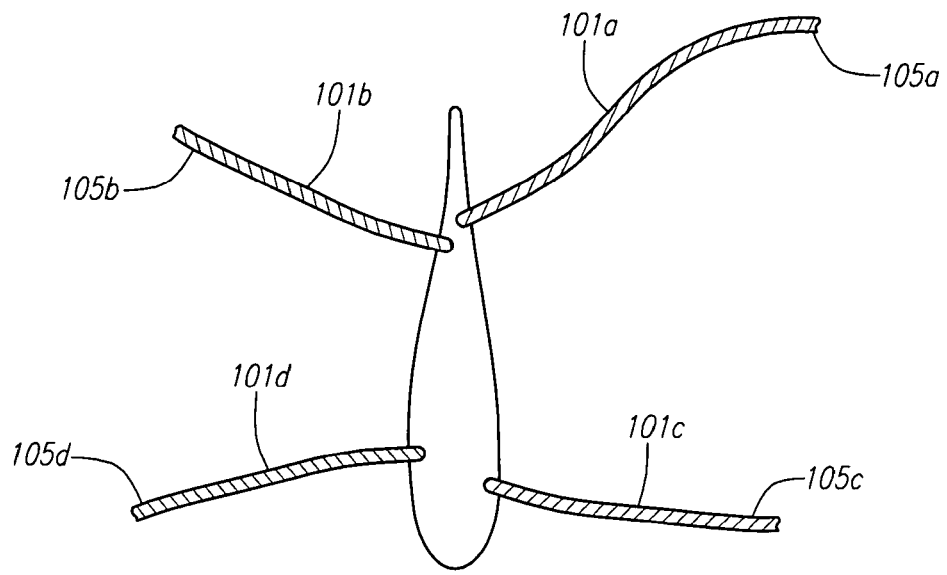
FIG. 4 is posterior view of the surgical incision with the mesh patch advanced into the wound.

FIG. 4 is posterior view of the surgical incision drawn in FIG. 2A. Mesh patch 110 has been advanced into the wound by pulling on free ends 105a-d of sutures 101a-d.

Figure 5A:
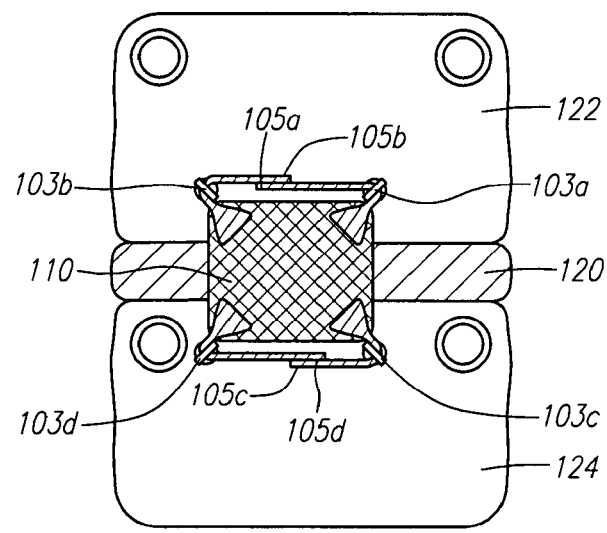
FIG. 5A is a posterior view of a coronal cross section of the spine with a mesh patch attached via suture anchors.

FIG. 5A is a posterior view of a coronal cross section of the spine and the embodiment of the invention drawn in FIG. 2A. The spine has been bisected through the pedicles of the vertebrae. Two anchors 103a-b have been inserted into the vertebra 122 cranial (towards the head) to the disc 120 and two anchors 103c-d have been inserted into the vertebra 124 caudal (towards the feet) to the disc 120. The free ends 105a-b of the sutures that pass through the anchors 103a-b in the cranial 122 vertebra were welded to each other and the free ends 105c-d of the sutures that pass through the anchors 103c-d in the caudal vertebra 124 were welded to each other. Tension is applied to the ends of the sutures before welding or otherwise connecting the ends of the sutures. Mesh patch 110 is smaller than the area between the four anchors 103a-d. The mesh patch could be smaller than the distance between the anchors by a ratio of 4:5. For example, if the distance between the anchors in the same vertebra is about 10 mm and the distance between anchors in the adjacent vertebra is about 15 mm, a rectangular mesh patch would preferably be about 8 mm×12 mm. Alternatively, the ratio may be about 4.5:5, alternatively about 3.5:5, alternatively about 3.0:5, alternatively about 2.5:5. The size of the mesh patch could be determined by the pair of suture anchors that are closest together in the vertical and the horizontal directions. The configuration enables the welded sutures 101a-d to apply tension to the four corners of mesh patch 110.

Figure 5B:
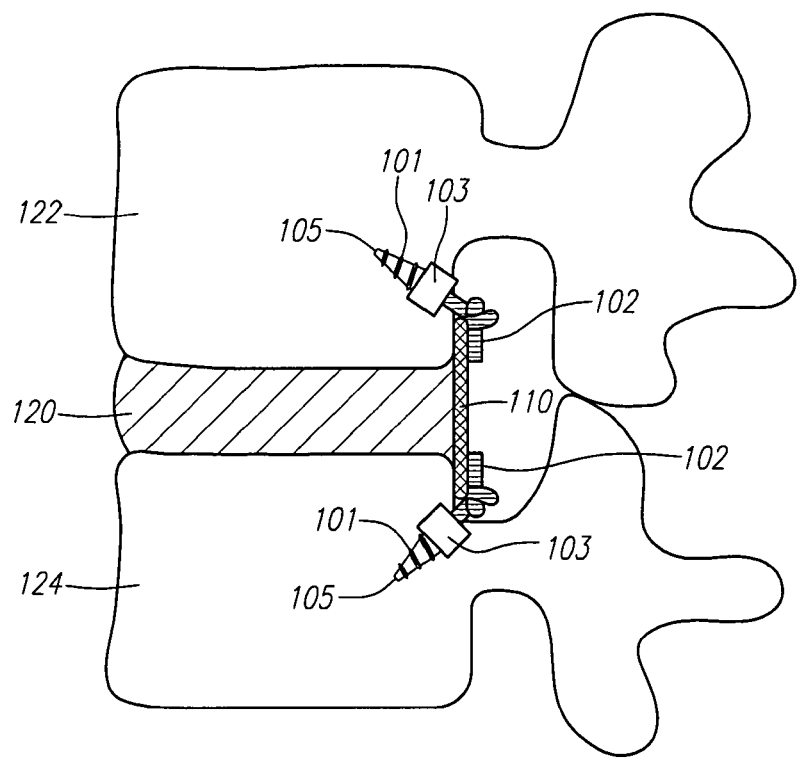
FIG. 5B is a lateral view of the spine and the embodiment of the invention drawn in FIG. 5A.

FIG. 5B is a lateral view of the spine and the embodiment of the invention drawn in FIG. 5A.

Figure 6A:
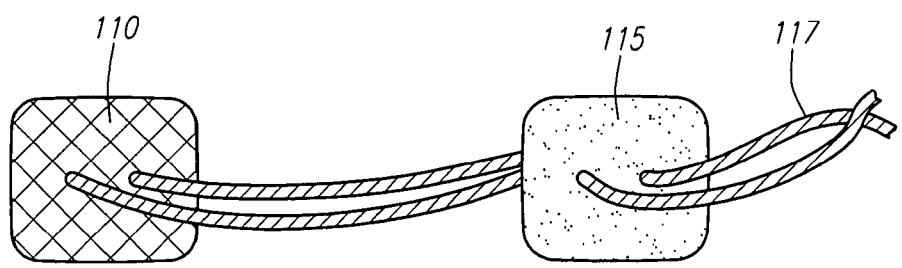
FIG. 6A is an oblique view of a portion of a mesh device loosely connected to an anti-adhesion cover.

FIG. 6A is an oblique view of a portion of the alternative mesh device described in FIG. 2B. Suture 117, such as a 2-0 nylon suture, loosely connects mesh patch 110 and anti-adhesion cover 115. For example, the anti-adhesion cover could be a sheet of ePTFE that is attached to the mesh patch 110. Anti-adhesion cover 115 has a thickness of preferably about 0.4 mm or less, alternatively about 0.3 mm or less. Anti-adhesion cover 115 preferably has a pore size that inhibits tissue in-growth. The interstices of anti-adhesion cover 115 may be approximately 3.0 microns, alternatively approximately 3.5 microns, alternatively approximately 4.0 microns. Suture 117 is preferably made of a monofilament suture in order to reduce the risk of adhesions. The device is preferably supplied to hospitals in the assembled configuration.

Figure 6B:
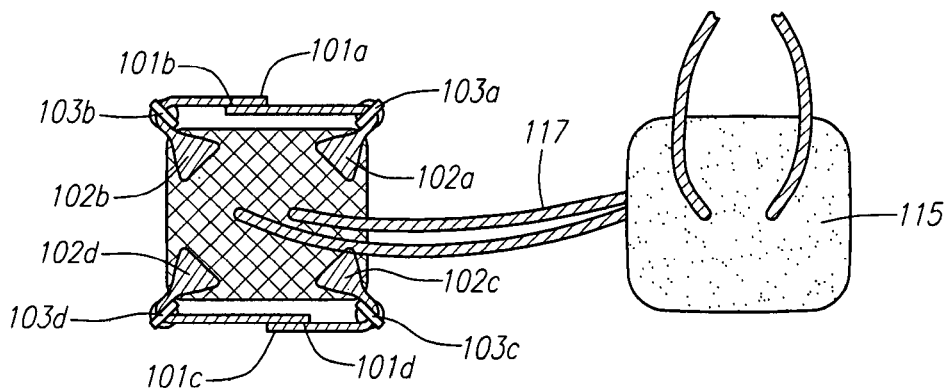
FIG. 6B is a posterior view of the embodiment drawn in FIG. 6A with the anti-adhesion cover held outside the wound as the mesh patch is fastened to the spine using sutures and anchors.

FIG. 6B is a posterior view of the embodiment of the invention drawn in FIGS. 2B and 6A. Anti-adhesion cover 115 is held outside the wound as mesh patch 110 is fastened to the spine using sutures 101a-d and anchors 103a-d.

Figure 6C:
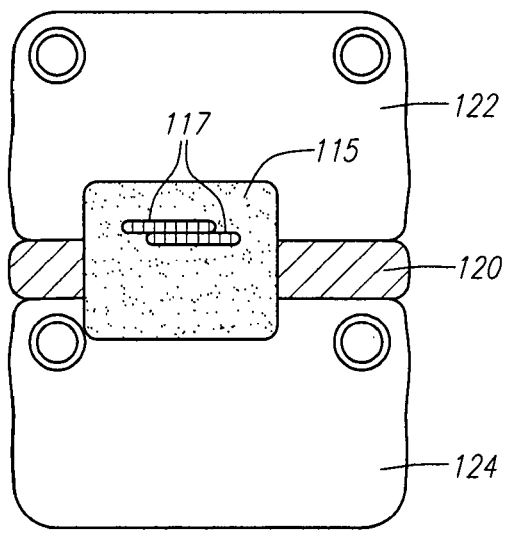
FIG. 6C is a posterior view of a coronal cross section of the spine with an anti-adhesion component covering the mesh patch and attached with sutures.

FIG. 6C is a posterior view of a coronal cross section of the spine and the embodiment of the invention drawn in FIG. 6B. The ends of suture 117 have been welded together. Anti-adhesion cover 115 covers mesh patch (not shown) and the attached sutures 101. The invention reduces the risk of adhesions to the nerves within the spinal canal.

Figure 6D:
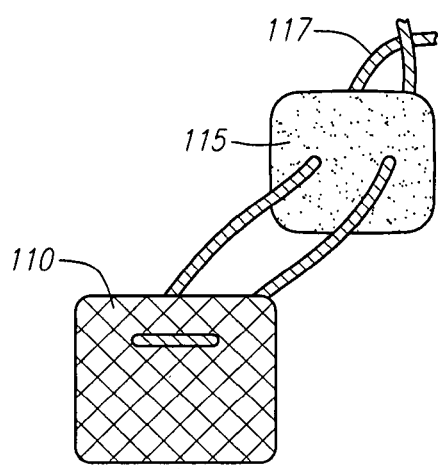
FIG. 6D is a view of the undersurface of the mesh patch and the anti-adhesion cover connected through a loop or stitch of suture.

FIG. 6D is a view of the undersurface of mesh patch 110 and the anti-adhesion cover 115 connected through loop or stitch of suture 117 through the pores of mesh patch 110.

FIG. 7A is an oblique view of an alternative embodiment of the invention drawn in FIG. 6D. Anti-adhesion cover 115 has been fastened to mesh patch 110 at or near an edge of mesh patch 110. As seen in FIG. 7A, a stitch of suture 117 located near the edge of anti-adhesion cover 115 and mesh patch 110 can be used to connect them. Alternatively, the components may be fastened together with other technologies such as adhesives.

FIG. 7B is an oblique view of the undersurface of the embodiment of the invention drawn in FIG. 7A. The ends of suture 117 have been welded over or onto mesh patch 110.

FIG. 7C is a posterior view of the embodiment of the invention drawn in FIGS. 5A and 7A. Anti-adhesion cover 115 is connected or coupled to mesh device 110 along an edge. Mesh patch 110 has been connected to anchors 103a-d with welded sutures 101a-d. The device is opened like a book to enable welding of mesh patch 110 to sutures 101a-d.

FIG. 7D is a posterior view of a coronal cross section of the spine and the embodiment of the invention drawn in FIG. 7C. Anti-adhesion cover 115 has been folded over mesh patch 110 (not shown), much like closing a book.

FIG. 7E is a view of the undersurface of mesh patch 110 drawn in FIG. 7D. The drawing shows the free ends of suture 117 welded together. Placing the suture weld under mesh patch 110 may reduce the risk of adhesions.

Figure 8A:
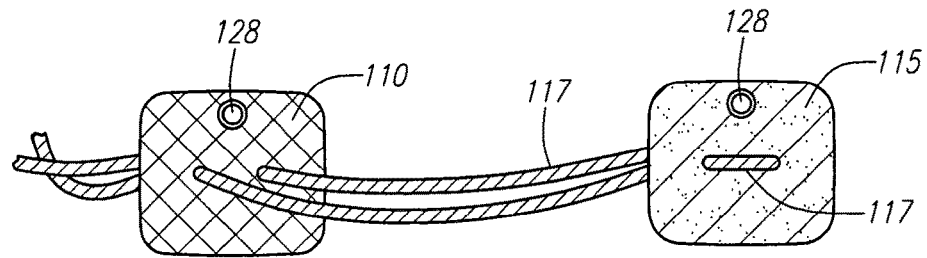
FIG. 8A is a posterior view of an alternative embodiment where the suture is threaded through anti-adhesion cover, such that the stitch or loop of suture is on the anti-adhesion cover.

FIG. 8A is a posterior view of an alternative embodiment of the invention drawn in FIG. 6B. In this embodiment, suture 117 is threaded through anti-adhesion cover 115, such that stitch or loop of suture 117 is on anti-adhesion cover 115. The ends of suture 117 extend from mesh patch 110 rather than anti-adhesion cover 115. Anti-adhesion cover 115 and mesh patch 110 may have a marking 128, such as a circle, to determine the orientation of the components.

Figure 8B:
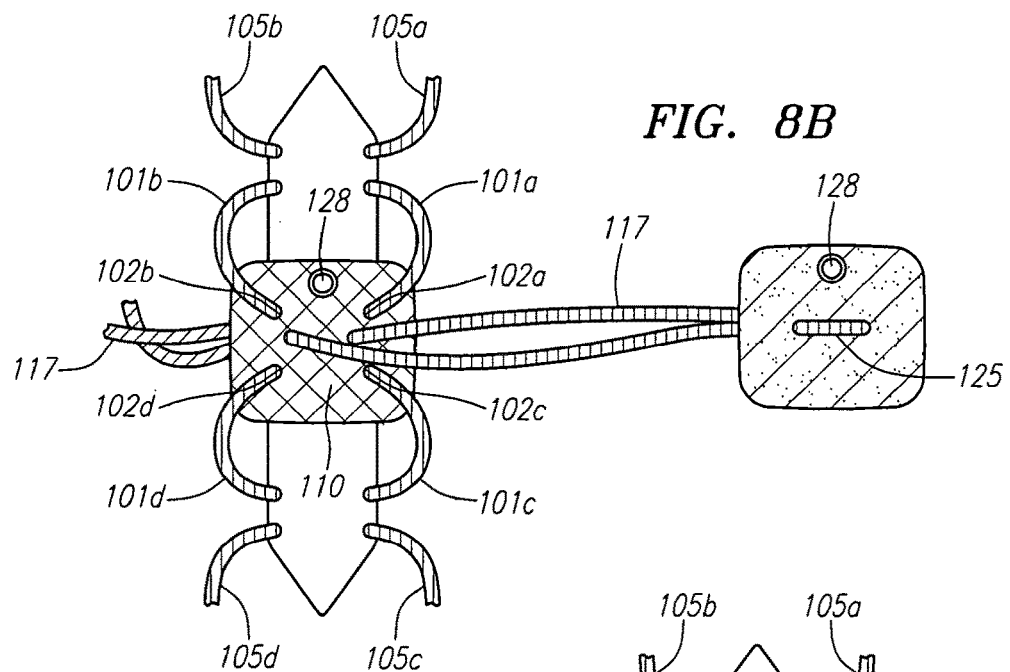
FIG. 8B is a posterior view of a surgical incision and the embodiment of the invention drawn in FIG. 8A with the ends of the sutures welded or otherwise fastened to the mesh patch.

FIG. 8B is a posterior view of a surgical incision and the embodiment of the invention drawn in FIG. 8A. Ends 102a-d of sutures 101a-d have been welded or otherwise fastened to mesh patch 110. Anchors 103a-d (not shown) have also been attached to the surrounding vertebra.

Figure 8C:
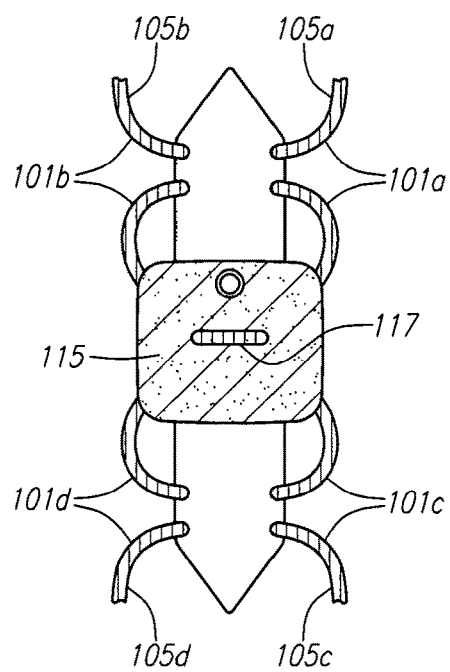
FIG. 8C is a posterior view of a surgical incision and the embodiment of the invention drawn in FIG. 8B with the anti-adhesion cover tightened and welded or otherwise secured over the mesh patch.

FIG. 8C is a posterior view of a surgical incision and the embodiment of the invention drawn in FIG. 8B. After welding the ends 102a-d (not shown) of the sutures to mesh patch 110 (not shown), suture 117 (not shown) connecting mesh patch 110 (not shown) and anti-adhesion cover 115 has been tightened and welded or otherwise secured. Anti-adhesion cover 115 and mesh patch 110 are fastened together before placing or tightening the assembled device onto the spine by pulling free ends 105a-d of sutures 101a-d through eyelets 104a-d (not shown) of anchors 103a-d (not shown).

Figure 8D:
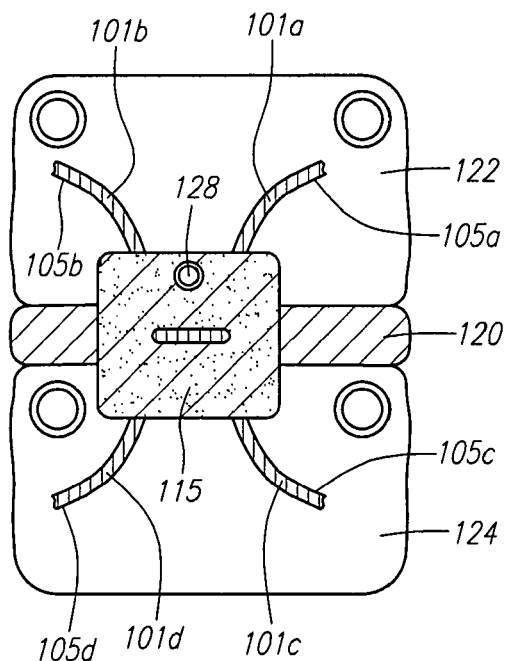
FIG. 8D is a posterior view of a coronal cross section of the spine and the embodiment of the invention drawn in FIG. 8C.

FIG. 8D is a posterior view of a coronal cross section of the spine and the embodiment of the invention drawn in FIG. 8C. Free ends 105a-d of sutures 101a-d can be seen extending beyond anti-adhesion cover 115.

Figure 8E:
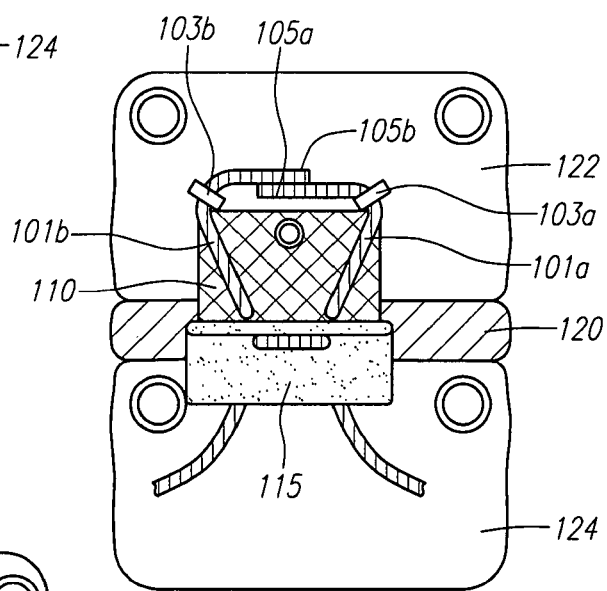
FIG. 8E is a posterior view of a coronal cross section of the spine and the embodiment of the invention drawn in FIG. 8D with the cranial half of the anti-adhesion cover folded in a caudal direction (towards the feet) to expose the mesh patch and the welded ends of sutures in the vertebra cranial to disc.

FIG. 8E is a posterior view of a coronal cross section of the spine and the embodiment of the invention drawn in FIG. 8D. The cranial half of anti-adhesion cover 115 has been folded in a caudal direction (towards the feet) to expose mesh patch 110 and the welded ends of sutures 101a-b in the vertebra 122 cranial to disc 120. The invention facilitates welding of sutures 101a-b from the anchors 103a-b in the vertebrae 122 cranial to disc 120. Tension is applied to free ends 105a-b of the sutures before welding the sutures.

Figure 8F:
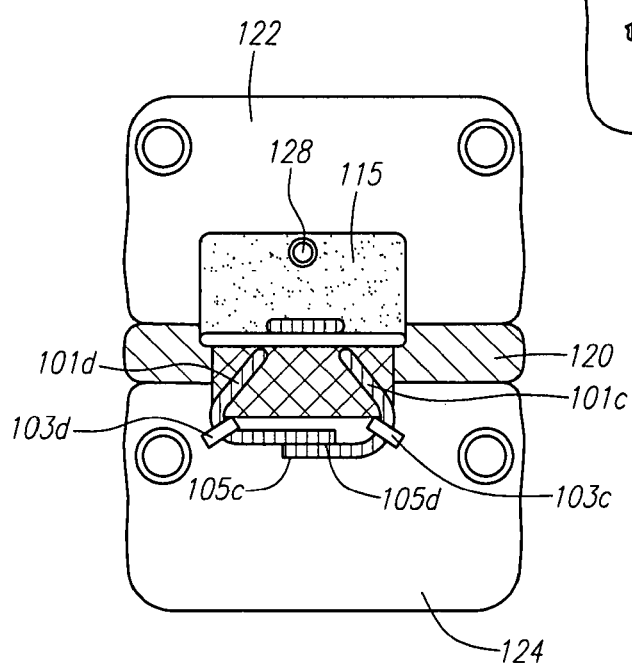
FIG. 8F is a posterior view of a coronal cross section of the spine and the embodiment of the invention drawn in FIG. 8E with the anti-adhesion cover folded in a cranial direction (towards the head) and the free ends of the sutures from the anchors in the vertebra caudal to disc welded together.

FIG. 8F is a posterior view of a coronal cross section of the spine and the embodiment of the invention drawn in FIG. 8E. Anti-adhesion cover 115 has been folded in a cranial direction (towards the head). Free ends 105c-d of the sutures from anchors 103c-d in the vertebra 124 caudal to disc 120 have been welded together. Welding fixation sutures 101c-d under tension applies tension to mesh patch 110. The distance between anchors 103c-d is greater than the length of mesh patch 110 in the vertical and horizontal directions.

Figure 8G:
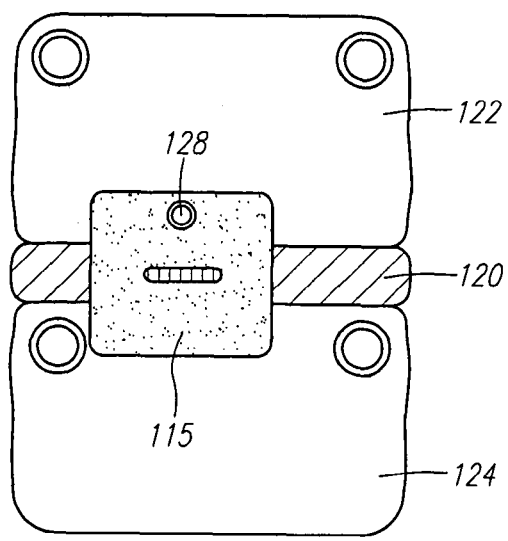
FIG. 8G is a posterior view of a coronal cross section of the spine and the embodiment of the invention drawn in FIG. 8F.

FIG. 8G is a posterior view of a coronal cross section of the spine and the embodiment of the invention drawn in FIG. 8F. Anti-adhesion patch 115 will have a larger size than mesh patch 110. This will enable complete coverage of welded sutures 101a-d and anchors 103a-d once it is deployed, thereby discouraging tissue in-growth and adhesions from outside the wound site. As seen in FIG. 8G, anti-adhesion cover 115 has been unfolded to cover mesh patch 110 (not shown), fixation sutures 101a-d (not shown), and anchors 103a-d (not shown).

Figure 9A:
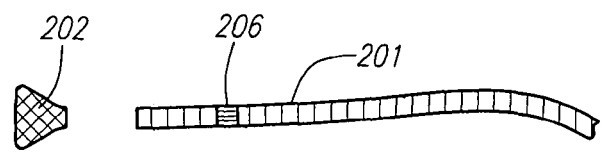
FIG. 9A is a posterior view of an exploded alternative embodiment of a suture including a component, such as a flattened mesh component, that is fastened to the end of the suture.

FIG. 9A is a posterior view of an exploded alternative embodiment of the suture drawn in FIG. 1. The invention includes component 202, such as a flattened mesh component, that is fastened to the end of suture 201. Component 202 could be welded or otherwise attached to the end of suture 201. Suture 201 has mark 206 that can be used to help surgeons determine the optimal place to weld suture 201 onto mesh patch 110.

Figure 9B:
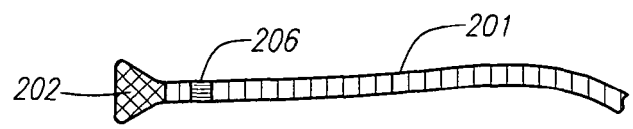
FIG. 9B is a posterior view of the embodiment of the invention drawn in FIG. 9A with the component attached to the end of the suture to increase the surface area of suture.

FIG. 9B is a posterior view of the embodiment of the invention drawn in FIG. 9A. Component 202 has been attached to the end of suture 201 to increase the surface area of suture 201.

Figure 9C:
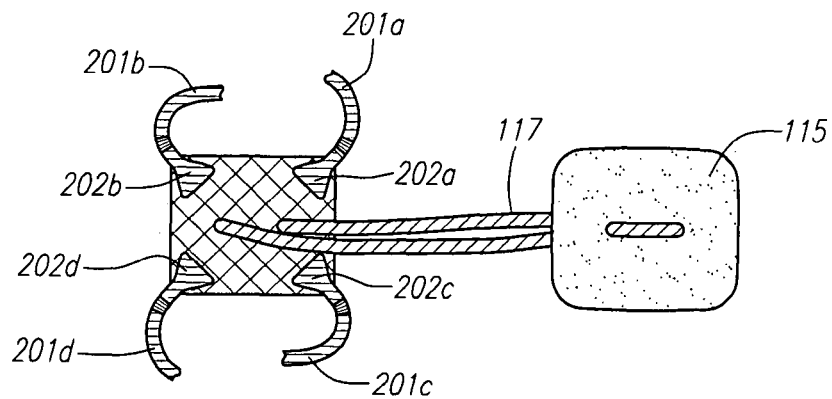
FIG. 9C is a posterior view of the embodiments of the invention drawn in FIGS. 8A and 9B with the enlarged ends of the sutures welded to the mesh patch.

FIG. 9C is a posterior view of the embodiments of the invention drawn in FIGS. 8A and 9B. Enlarged ends 202a-d of the sutures 201a-d have been welded to mesh patch 110.

Figure 9D:
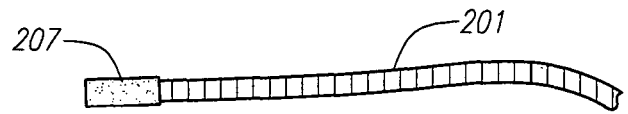
FIG. 9D is a lateral view of a portion of a suture covered with a biocompatible polymer sleeve.

FIG. 9D is a lateral view of a portion of an alternative embodiment invention drawn in FIG. 9A. The end of suture 201 is covered with biocompatible polymer sleeve 207. For example, sleeve 207 could be made of polyurethane, silicon, polyethylene, polyester, or other biocompatible material. The end of suture 201 distal to sleeve 207 could be enlarged in alternative embodiments of the invention (not shown). An enlarged end of the suture would increase the pullout resistance of the suture through polymer sleeve.

Figure 9E:
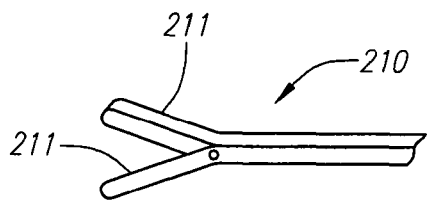
FIG. 9E is a lateral view of the tip of the instrument used to melt the polymer sleeve drawn in FIG. 9D.

FIG. 9E is a lateral view of the tip of instrument 210 used to melt the polymer sleeve 207 drawn in FIG. 9D. Instrument 207 is used outside the surgical incision. Jaws 211 of instrument 210 apply heat and pressure to the mesh patch and the tip of suture 201 drawn in FIG. 9D.

Figure 9F:
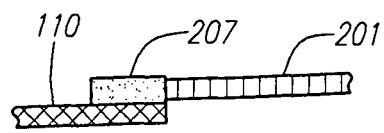
FIG. 9F is a lateral view of a portion of the mesh patch and the tip of suture with the sleeve drawn in FIG. 9D.

FIG. 9F is a lateral view of a portion of mesh patch 110 and the tip of suture 201 with sleeve 207 drawn in FIG. 9D.

Figure 9H:
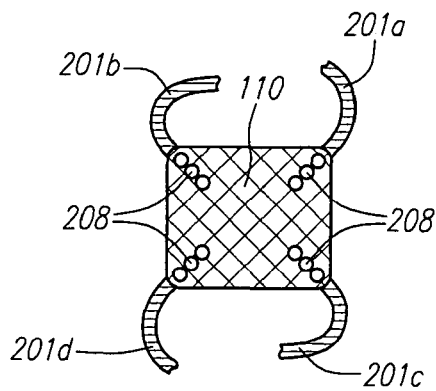
FIG. 9H is view of the embodiments of a mesh patch and sutures drawn in FIG. 9G.
Figure 9G:
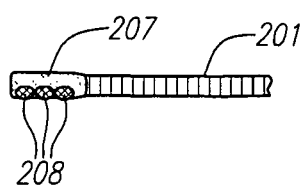
FIG. 9G is cross section of the embodiment of the mesh patch and the suture drawn in FIG. 9F.

FIG. 9G is cross section of the embodiment of mesh patch 110 and suture 201 drawn in FIG. 9F. Polymer sleeve 207 has been melted by instrument 210 drawn in FIG. 9E. The melted polymer 208 flowed and set within the porous mesh, thus attaching suture 201 to mesh patch 110. Alternatively, a melted polymer could be injected between suture and the mesh. The alternative embodiment would be similar to injecting hot glue with a "glue gun." The polymer could have adhesive properties or simply form a mechanical lock with the pores of the mesh patch.

FIG. 9H is view of the embodiments of mesh patch 110 and sutures 201a-d drawn in FIG. 9G, on the disc surface. The melted polymer 208 can be seen within the pores of mesh patch 110. The melted polymer could pass through adjacent pores and flow together, thus surrounding portions of mesh patch 110.

Figure 9I:
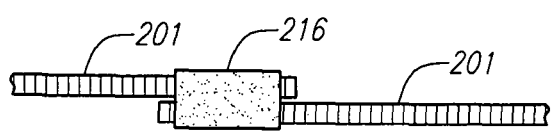
FIG. 9I is a lateral view of the ends of two sutures and a polymer sleeve having two holes that can be melted to connect the ends of the two sutures.

FIG. 9I is a lateral view of the ends of two sutures 201 and an alternative embodiment of the polymer sleeve drawn in FIG. 9D. Sleeve 216 has two holes. Sleeve 216 can be melted to connect the ends of two sutures 201.

Figure 10:
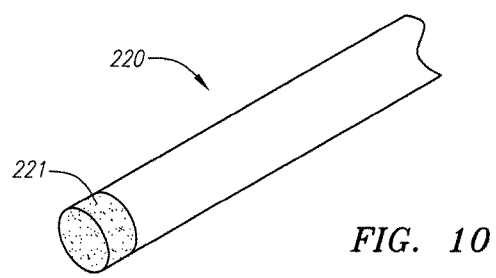
FIG. 10 is an oblique view of a tip of an instrument that may be used to create abrasions over the AF, vertebrae, and the periosteum.

FIG. 10 is an oblique view of tip 221 of instrument 220 that may be used to create abrasions over the AF, vertebrae, and the periosteum. Tip 221 is covered with an abrasive material such as a wire mesh or a wire brush.

Figure 11:
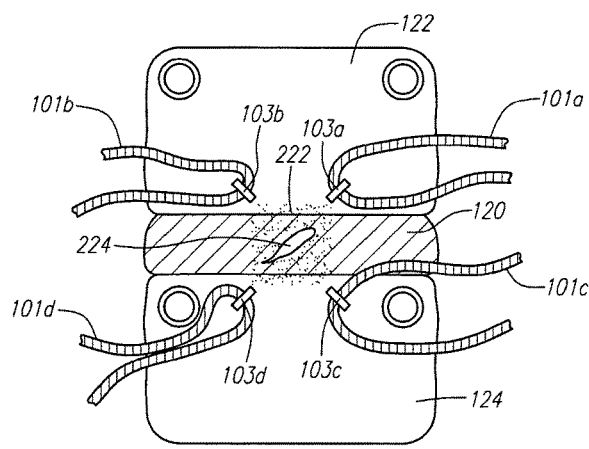
FIG. 11 is a posterior view of a coronal cross section of the spine, sutures from four anchors, and preferred area of abrasion surrounding and including the defective region within the anulus fibrosus of the disc.

FIG. 11 is a posterior view of a coronal cross section of the spine, sutures 101a-d from four anchors 103a-d, and preferred area of abrasion 222 surrounding and including defective region 224 within the anulus fibrosus of disc 120.

Figure 12A:
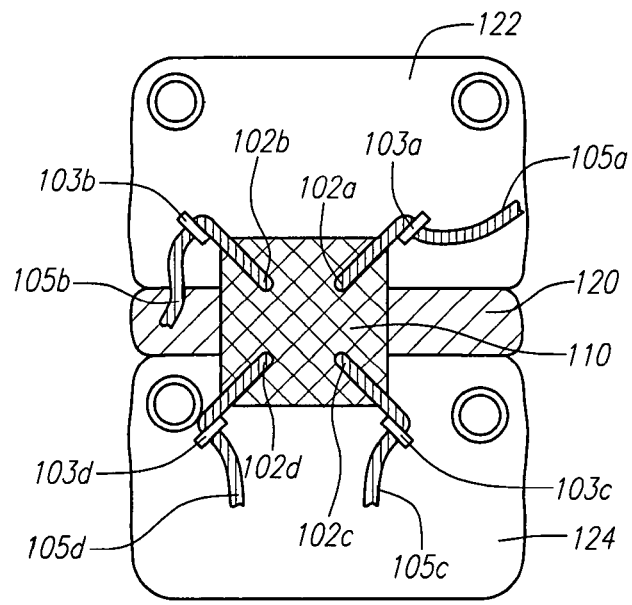
FIG. 12A is a posterior view of a coronal cross section of the spine and an alternative embodiment of the invention with the ends of the sutures welded or otherwise fastened to the mesh patch.

FIG. 12A is a posterior view of a coronal cross section of the spine and an alternative embodiment of the invention drawn in FIG. 5A. Ends 102a-d of the sutures are welded or otherwise fastened to mesh patch 110. Free ends 105a-d of the sutures can be seen extending through eyelets 104a-d (not shown) in anchors 103a-d.

Figure 12B:
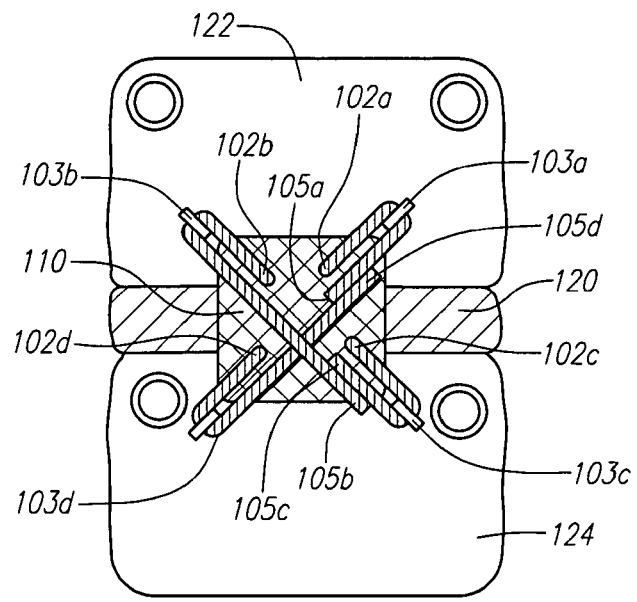
FIG. 12B is a posterior view of a coronal cross section of the spine and the embodiment of the invention drawn in FIG. 12A with the free ends of the sutures welded to the free ends of the sutures anchored to the adjacent vertebra rather than to the sutures from the same vertebra.

FIG. 12B is a posterior view of a coronal cross section of the spine and the embodiment of the invention drawn in FIG. 12A. Free ends 105a-d of the sutures were welded to the free ends of the sutures anchored to the adjacent vertebra rather than to the sutures from the same vertebra. For example, where sutures 101a and b are anchored to vertebrae 122 cranial to disc 120 and sutures 101c and d are anchored to vertebrae 124 caudal to disc 120, free ends 105a and 105d are welded together and free ends 105b and 105c are welded together. The sutures could be relatively elastic to allow spinal movement across the disc. Alternatively, in-elastic sutures could be used to restrict spinal flexion and axial rotation across the disc. Restricting spinal motion reduces the pressure on the defective region of the AF.

Figure 13A:
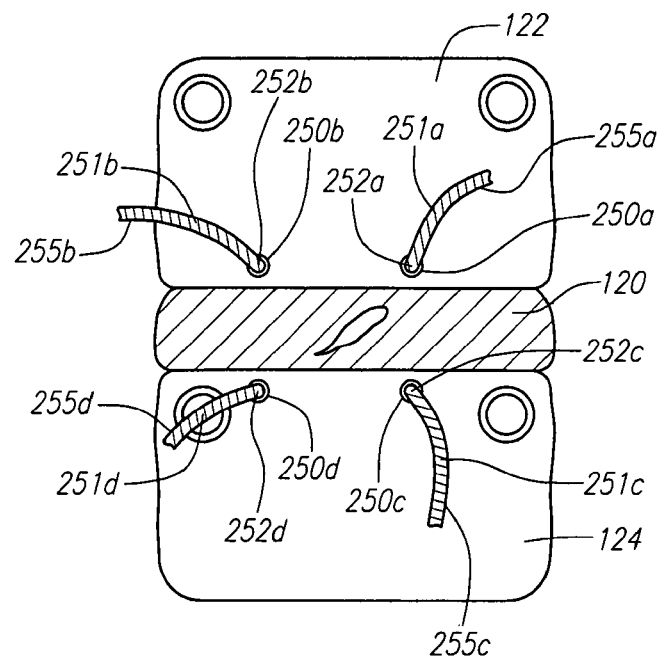
FIG. 13A is a posterior view of a coronal cross section of the spine and an alternative embodiment of the invention including suture assemblies with sutures having first ends that are attached or connected to anchors and second or free ends.

FIG. 13A is a posterior view of a coronal cross section of the spine and an alternative embodiment of the invention drawn in FIG. 12A. The suture assemblies of this invention comprise sutures 251a-d having first ends 251a-d and second or free ends 255a-d. First ends 251a-d are attached or connected to anchors 250a-d. Anchors 250a-b are inserted into or otherwise attached to vertebrae 122 cranial to disc 120. Anchors 250c-d are inserted into or otherwise attached to vertebrae 124 caudal to disc 120.

Figure 13B:
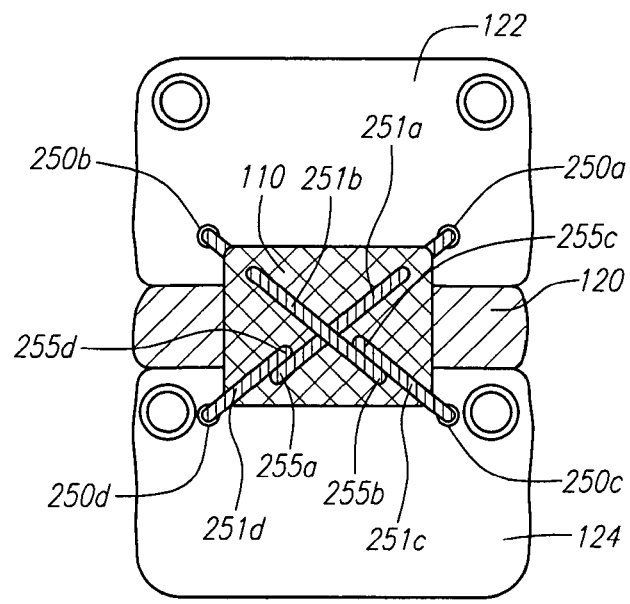
FIG. 13B is a posterior view of a coronal cross section of the spine and the embodiment of the invention drawn in FIG. 13A where the free ends of the sutures were welded to each other over the mesh patch.

FIG. 13B is a posterior view of a coronal cross section of the spine and the embodiment of the invention drawn in FIG. 13A. Free ends 255a-d of the sutures were welded to each other over mesh patch 110. Two of the sutures, for example, sutures 251a and b or sutures 251c and d, pass through mesh patch 110. The sutures may pass through a reinforced portion (not shown) of mesh patch 110. Sutures 251a-d are not welded to mesh patch 110 in this embodiment of the invention.

Figure 14A:
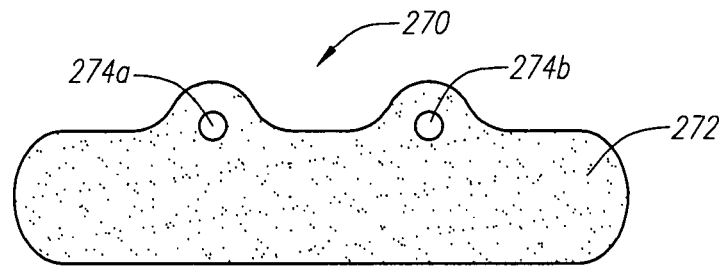
FIG. 14A is a posterior view of a support structure comprising a body and eyelets.

FIG. 14A is a posterior view of an alternative embodiment of the invention. Support structure 270 comprises body 272 and eyelets 274a-b. The number of holes or eyelets 274 may vary depending on the number of sutures present. There may be 2 holes or eyelets, alternatively 3 holes or eyelets, alternatively 4 holes or eyelets, alternatively 5 holes or eyelets, alternatively 6 holes or eyelets. Eyelets 274 are adapted to receive sutures 251 therethrough. Support structure 270 is preferably stiffer than the porous mesh and is able to provide more structural support. Support structure 270 serves to reinforce mesh patch 110. Support structure 270 could be made of absorbable materials such as Hydrosorb (Macropore, San Diego, Calif.) or non-absorbable materials such as PEEK or polyethylene.

Figure 14B:
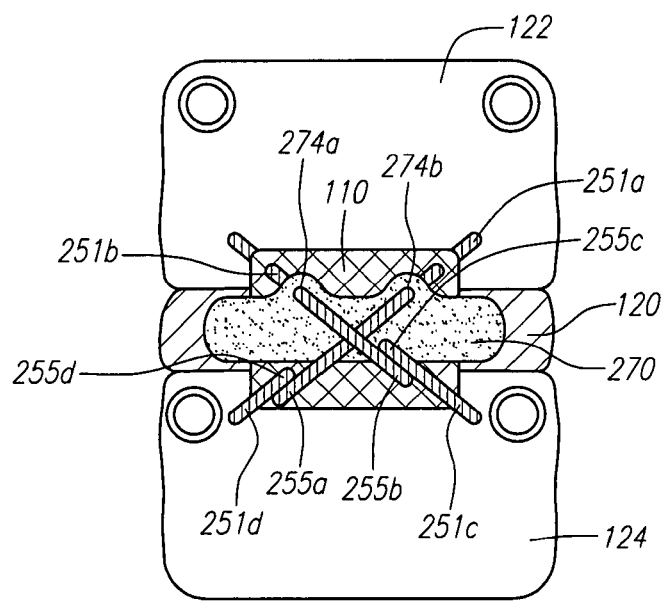
FIG. 14B is a posterior view of a coronal cross section of the spine with a mesh patch and associated sutures where the sutures pass through the eyelets of the support structure.

FIG. 14B is a posterior view of a coronal cross section of the spine and the embodiments of the invention drawn in FIGS. 14A and 13B. Sutures 251a-b pass through eyelets 274a-b. Free ends 255a and d are welded together or otherwise attached. Similarly, free ends 255b and c are welded together or otherwise attached.

Figure 15A:
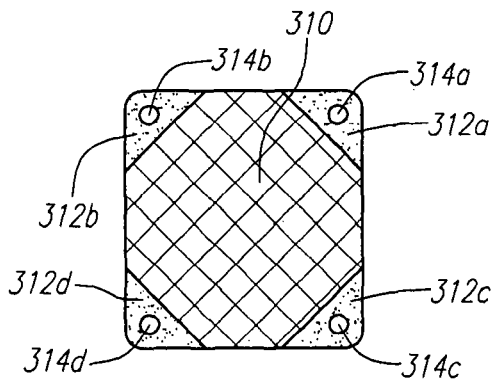
FIG. 15A is an anterior view of an alternative embodiment of the mesh patch having reinforced corners with holes or eyelets.

FIG. 15A is an anterior view of an alternative embodiment of the mesh patch drawn in FIG. 2A. The corners 312a-d of mesh patch 310 are reinforced and have holes or eyelets 314a-d.

Figure 15B:
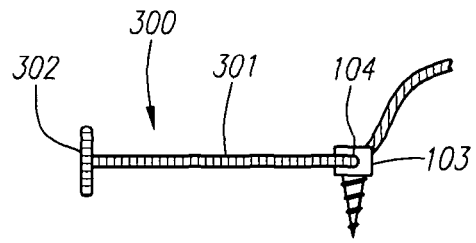
FIG. 15B is a lateral view of a suture anchor having a suture with a stiff component and screw (or anchor).

FIG. 15B is a lateral view of suture anchor 300, an alternative embodiment of the invention drawn in FIG. 1. Suture anchor 300 comprises suture 301 with stiff component 302 and screw (or anchor) 103. Anchor 103 has a first portion capable of being inserted into or otherwise attached to a bone, such as a vertebra. Anchor 103 also has a second portion with an opening 104 adapted to receive a suture therethrough. In one embodiment, anchor 103 is a screw having a hole through the head of screw. Suture 301 is threaded through hole 104. Suture 301 is preferably made of polyester or other weldable material and has a break-strength of greater than about 22 lbs. Screw or anchor 103 is preferably about 3 mm in diameter, alternatively about 4 mm in diameter, and between about 5 mm and about 10 mm in length. However, alternative sized sutures or screws may be used with this invention. Anchors 103 are preferably made of a MRI compatible and radio-opaque material such as Titanium. Plastic or bioresorbable anchors may also used with this invention. Anchors 103 are preferably self-drilling and self-tapping. Stiff component (or enlarged or transverse component) 302 is attached to one end of suture 301. The ends of stiff component 302 are blunt to prevent penetration into or injury of the nerves or disc. Stiff component 302 is attached at angle, preferably about ninety degrees, alternatively about 85 degrees, alternatively about 80 degrees, alternatively about 75 degrees, alternatively about 70 degrees, alternatively about 60 degrees, relative to a longitudinal axis of a region of suture 301 near or adjacent to stiff component 302. Holes or eyelets 314 are adapted to receive stiff component 302 therethrough. Stiff component (or transverse component 302) may be a T-anchor.

Figure 15C:
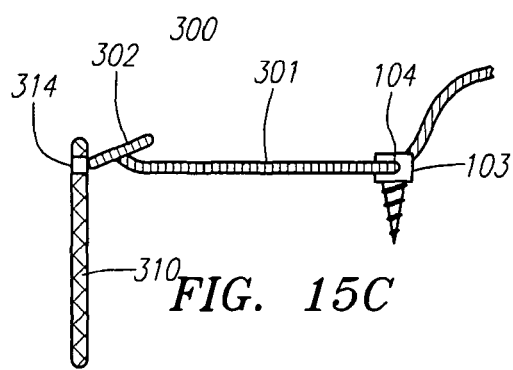
FIG. 15C is a lateral view of the embodiments of the invention drawn in FIGS. 15A and 15B with the stiff or transverse component adjacent to the eyelet in the mesh patch.

FIG. 15C is a lateral view of the embodiments of the invention drawn in FIGS. 15A and 15B. Stiff or transverse component 302 is adjacent to eyelet 314 in mesh patch 310. The flexibility of suture 301 allows the angle between the suture and stiff or transverse component 302 to vary between about 90 degrees and about 180 degrees. In other words, in a resting state and/or when deployed, stiff or transverse component 302 is substantially non-parallel, or approximately perpendicular, to a longitudinal axis of a region of the suture near or adjacent to the point of attachment of stiff or transverse component 302 and suture 301. Stiff or transverse component 302 can, however, be manipulated for delivery such that its longitudinal axis is substantially parallel to the longitudinal axis of a region of the suture near or adjacent to the point of attachment of stiff or transverse component 302 and suture 301. Changing the angle between suture 301 and stiff component 302 facilitates insertion of stiff component 302 through eyelet 314 in mesh patch 310. Stiff components 302 of four sutures are placed through mesh patch 310 outside the surgical incision in the preferred embodiment of the device.

Figure 15D:
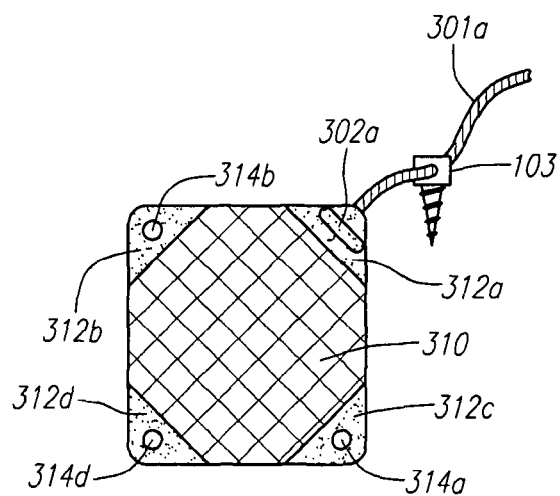
FIG. 15D is a posterior view of the embodiments of the invention drawn in FIG. 15C with the stiff or transverse component placed through the eyelet.

FIG. 15D is a posterior view of the embodiments of the invention drawn in FIG. 15C. Stiff or transverse component 302a has been placed through eyelet 314a (not shown) in mesh patch 310. Stiff component 302a prevents suture 301a from pulling out of mesh patch 310 when tension is applied to the suture.

Figure 15E:
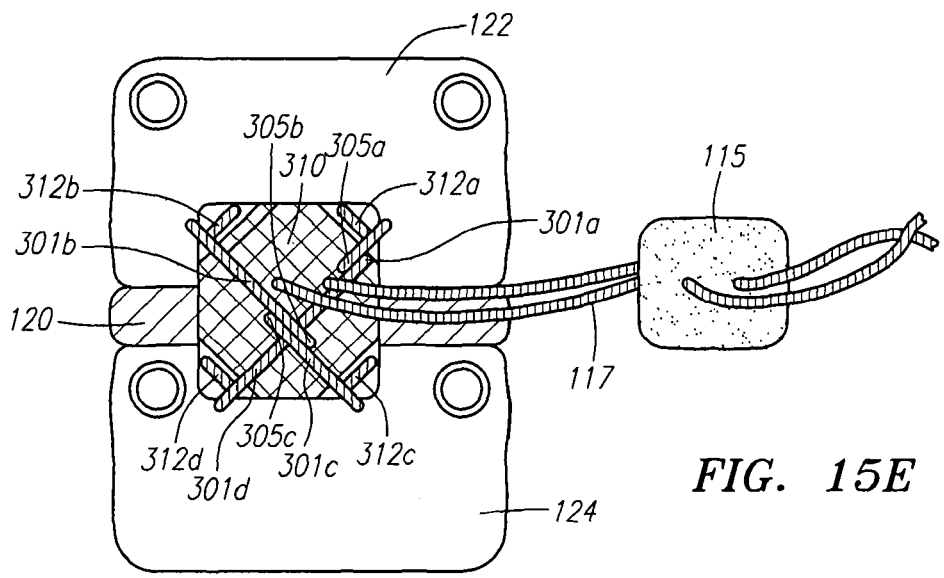
FIG. 15E is a posterior view of a coronal cross section of the spine and the embodiment of the invention drawn in FIG. 15D with four sutures placed through the corners of the mesh patch.

FIG. 15E is a posterior view of a coronal cross section of the spine and the embodiment of the invention drawn in FIG. 15D. Four sutures 301a-d have been placed through corners 312a-d of mesh patch 310. As described in the text of FIG. 12B, the second ends 305a-d of the sutures have been welded or otherwise fastened to each other under tension. Anti-adhesion cover 115 can be seen connected to mesh patch 310 through suture 117.

In an alternative embodiment (not shown), anti-adhesion cover 115 could be laminated to mesh patch 310. Stiff components 302 from the suture anchors could be passed through eyelets in mesh patch 310 and anti-adhesion cover 115. The second ends of sutures 301a-d could be welded over the combined mesh patch/anti-adhesion cover. The alternative embodiment provides a tighter seal of the disc. The tight seal helps prevent the extrusion of the NP and the escape of liquids, gels, or other therapeutic material that may be placed into the disc. Alternative materials, such as Dual Mesh (W.L. Gore and Associates, Flagstaff, Ariz.), with anti-adhesion and tissue in-growth sides on a single patch component could be used the alternative embodiment of the invention. The second ends of the sutures 301a-d may be welded in various configurations that help seal liquids or gels within the disc. Mesh patches with smaller pores could be also be used to seal the disc. The mesh patch could have variable porosity. For example, the mesh patch could have large pores (about 1000 microns) around the periphery of the mesh patch and small pores (less than about 999 microns to about 3 microns) directly in the center of the mesh. The configuration encourages tissue in-growth over the portion of the device that overlies intact regions of the AF and seals the disc over portion of the device that overlies an aperture or defective regions of the AF. Bio-glues, such as Tisseal, may be placed between the patch and the AF to help seal the disc. Lastly, the anti-adhesion cover may be used without the mesh patch component in embodiments of the invention that are designed to seal the disc.

FIG. 16A is an exploded lateral view of an alternative embodiment of the invention drawn in FIG. 15C. Stiff component 302 is attached to one end of suture 301 after passing one end of suture 301 through eyelet 104 in reinforced mesh patch 310. Stiff component 302 may be welded to suture 301. Alternative methods may be used to fasten the components including but not limited to the use of adhesives, press-fit components, or the use of plastic components that snap together. The components are fastened together outside the surgical wound.

FIG. 16B is a posterior view of the embodiment of the invention drawn in FIG. 16A.

FIG. 17 is a posterior view of an alternative embodiment of the invention drawn in FIG. 16B. Four sutures 301a-d with enlargements 322a-d at the first ends of the sutures are passed through eyelets 314a-d (not shown) in the corners of mesh patch 310 then passed through eyelets 104a-d in anchors 103a-d. Anchors 103a-d are placed into the vertebrae after assembling the components. Enlarged ends 322a-d of the sutures are rotated in the opposite directions that screws 103a-d were rotated to remove the twists that occur in sutures 301a-d during anchor insertion. Sutures 301a-d freely rotate with eyelets 314a-d of mesh patch 310. A tool, such as a wire twister, may be used to grasp and counter rotate the sutures. The second ends (or free ends) 305a-d of the sutures are fastened to each other as previously described, after the sutures are counter-rotated.

FIG. 18A is a lateral view of an alternative embodiment of the invention drawn in FIG. 15B. One end of suture 301 has deformable component 332. One or more arms of deformable component 332 bend in one direction easier than they bend in a second direction.

FIG. 18B is a lateral view of mesh patch 310 and the embodiment of the invention drawn in FIG. 18A. Deformable end 332 of the suture was passed through opening 314 in mesh patch 310. The shape of deformable component 332 allows the component to be passed through a hole in the mesh.

FIG. 18C is a lateral view of the embodiment of the invention drawn in FIG. 18B. Tension has been applied to free end 305 of suture 301. Deformable component 332 prevents suture 301 from pulling out of mesh patch 310. Deformable component 332 resists bending beyond about ninety degrees. Shape memory materials, such as Nitinol, or elastic materials, such as plastics or metals may be used in this embodiment of the invention.

Although the foregoing invention has, for the purposes of clarity and understanding, been described in some detail by way of illustration and example, it will be obvious that certain changes and modifications may be practiced which will still fall within the scope of the appended claims.

The invention claimed is:

1. A method of treating a defect in a vertebral disc of a patient, the method comprising:
    providing a device comprising:
        a mesh patch;
        first, second, third, and fourth sutures, each having a first end and a second end; and
        first, second, third, and fourth anchors, each adapted for insertion into a vertebral body adjacent the vertebral disc, wherein the first ends of the first, second, third, and fourth sutures are capable of being coupled to the first, second, third, and fourth anchors, respectively;
    inserting the first and second anchors into a vertebral body cranial to the vertebral disc;
    inserting the third and fourth anchors into a vertebral body caudal to the vertebral disc;
    attaching the first ends of the first, second, third, and fourth sutures to the first, second, third, and fourth anchors, respectively;
    positioning the mesh patch against the defect in the vertebral disc by pulling on the second end of the first, second, third, and fourth sutures; and
    attaching the second end of the first suture to the second end of the third suture over the mesh patch, and attaching the second end of the second suture to the second end of the fourth suture over the mesh patch, whereby to capture the mesh patch against the defect in the vertebral disc;
    wherein the second end of the first suture is attached to the second end of the third suture so as to form a substantially continuous band of suture extending over the mesh patch from the first anchor to the third anchor, and the second end of the second suture is attached to the second end of the fourth suture so as to form a substantially continuous band of suture extending over the mesh patch from the second anchor to the fourth anchor, and further wherein the substantially continuous band of suture extending from the first anchor to the third anchor crosses the substantially continuous band of suture extending from the second anchor to the fourth anchor.

2. The method of claim 1, further comprising the step of placing an anti-adhesion cover adjacent the mesh patch.

3. The method of claim 2, wherein the anti-adhesion cover is connected to the mesh patch.

4. The method of claim 1, wherein the first, second, third and fourth sutures further comprise a transverse element and wherein the mesh patch comprises first, second, third and fourth openings, wherein the method further comprises inserting the first, second, third and fourth sutures through the first, second, third and fourth openings, respectively, such that the transverse elements are positioned on a side of the mesh patch opposite of the second ends of the first, second, third and fourth sutures.

5. The method of claim 4, wherein upon insertion into the first, second, third and fourth openings, a longitudinal axis of the transverse elements is substantially perpendicular to a longitudinal axis of the first, second, third and fourth sutures near the first ends.

6. The method of claim 1, wherein the second end of the first suture is attached to the second end of the third suture by welding.

7. The method of claim 1, wherein the second end of the second suture is attached to the second end of the fourth suture by welding.

8. The method of claim 1, wherein the second ends of the first, second, third, and fourth sutures are attached by welding.

9. The method of claim 1, wherein the first, second, third and fourth sutures are slideably attached to the first, second, third and fourth anchors, respectively.

10. The method of claim 1, wherein the first, second, third and fourth sutures are fixedly attached to the first, second, third and fourth anchors, respectively.

* * * * *